(12) United States Patent
Shen et al.

(10) Patent No.: US 10,640,592 B2
(45) Date of Patent: May 5, 2020

(54) CATION POLYMER CAPABLE OF REMOVING POSITIVE CHARGES THROUGH OXIDATIVE RESPONSE, A PREPARATION METHOD AND APPLICATION

(71) Applicant: ZHEJIANG UNIVERSITY, Hangzhou, Zhejiang Province (CN)

(72) Inventors: Youqing Shen, Hangzhou (CN); Xin Liu, Hangzhou (CN); Jianbin Tang, Hangzhou (CN); Xiangrui Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/768,470

(22) PCT Filed: Oct. 13, 2015

(86) PCT No.: PCT/CN2015/091803
§ 371 (c)(1),
(2) Date: Apr. 13, 2018

(87) PCT Pub. No.: WO2017/063131
PCT Pub. Date: Apr. 20, 2017

(65) Prior Publication Data
US 2018/0312617 A1 Nov. 1, 2018

(51) Int. Cl.
| | | |
|---|---|---|
| *C08F 120/36* | (2006.01) | |
| *C08F 8/12* | (2006.01) | |
| *C08F 8/42* | (2006.01) | |
| *A61K 47/58* | (2017.01) | |
| *C08F 8/44* | (2006.01) | |
| *C12N 15/88* | (2006.01) | |
| *C08F 130/06* | (2006.01) | |
| *A61K 47/59* | (2017.01) | |
| *C08F 8/06* | (2006.01) | |
| *C08F 120/34* | (2006.01) | |
| *C08G 83/00* | (2006.01) | |
| *A61K 31/337* | (2006.01) | |
| *C08G 73/02* | (2006.01) | |
| *A61K 48/00* | (2006.01) | |

(52) U.S. Cl.
CPC .......... *C08F 120/36* (2013.01); *A61K 31/337* (2013.01); *A61K 47/58* (2017.08); *A61K 47/585* (2017.08); *A61K 47/59* (2017.08); *A61K 47/595* (2017.08); *C08F 8/06* (2013.01); *C08F 8/12* (2013.01); *C08F 8/42* (2013.01); *C08F 8/44* (2013.01); *C08F 120/34* (2013.01); *C08F 130/06* (2013.01); *C08G 73/0206* (2013.01); *C08G 73/028* (2013.01); *C08G 83/004* (2013.01); *C12N 15/88* (2013.01); *A61K 48/0041* (2013.01)

(58) Field of Classification Search
CPC ...... C08F 8/06; C08F 8/12; C08F 8/42; C08F 8/44; C08F 120/36; C08F 120/34; C08F 130/06; C08G 73/0206; C08G 73/028; C08G 83/004
See application file for complete search history.

(56) References Cited

FOREIGN PATENT DOCUMENTS

| | | |
|---|---|---|
| CN | 101597349 A | 12/2009 |
| CN | 101659722 A | 3/2010 |
| WO | WO2004065440 A | 8/2004 |
| WO | WO 2017/063131 A1 * | 4/2017 |

OTHER PUBLICATIONS

Machine translation of Description and Claims of WO 2017/063131; Apr. 2017.*
https://en.wikipedia.org/wiki/Acyl_group; Nov. 2018.*

* cited by examiner

*Primary Examiner* — Edward J Cain
(74) *Attorney, Agent, or Firm* — Jiwen Chen (57) ABSTRACT

Disclosed are the cation polymers capable of removing their positive charges in oxidative conditions, preparation methods, and applications as gene delivery carriers. The oxidation-responsive unit is the p-(boronic acid or ester)benzylammonium, which upon oxidation eliminates p-hydroxymethlphenol and thus converts in a tertiary amine. Compared with the prior art, different from a common quaternary amination carrier, the synthesized charge reversal type gene delivery carrier for oxidative response of the present invention has a large quantity of positive charges and can well coat a DNA, but the positive charges can be removed under the condition of intracellular oxidation when the charge reversal type gene delivery carrier enters a cell, a charge reverse is triggered, the positive charges turn to negative charges, and the DNA is quickly released for transfection. The carrier is efficient, low in toxicity, and good in application prospect.

5 Claims, 6 Drawing Sheets

CATION POLYMER CAPABLE OF REMOVING POSITIVE CHARGES THROUGH OXIDATIVE RESPONSE, A PREPARATION METHOD AND APPLICATION

This is a U.S. national stage application of PCT Application No. PCT/CN2015/091803 under 35 U.S.C. 371, filed Oct. 13, 2015 in Chinese, which is hereby incorporated by reference.

FIELD OF INVENTION

The present invention belongs to the field of polymer and biotechnology. Particularly, the present invention relates to cation polymers capable of removing their positive charges through oxidative response, the preparation methods and the applications as gene delivery carriers.

BACKGROUND OF INVENTION

Gene therapy has emerged as a new approach treating genetic disorders by delivering therapeutic genes to targeted diseased tissues, and has been proven to be an effective approach for cancer treatments with few side effects. The currently used gene vectors can be divided into viral vectors and non-viral vectors. Non-viral gene vectors including cationic lipids, polymers, dendrimers and peptides are particularly attractive in terms of safety, low immunogenicity, biocompatibility, and the potential for large-scale manufacture. However, their applications are bottlenecked by low transfection efficiency compared with viral vectors.

In nonviral gene delivery, cationic polymers are generally used to neutralize the negative charges of DNA and condense the large macromolecules into nanoparticles to protect them from DNA degradation and facilitate its cellular internalization. However, DNA/polymer complexes (polyplexes) are thermodynamically stable and inherently resistant to dissociation, which is necessary to release the DNA for transcription once inside the cell. Therefore, smart designs are required to facilitate DNA release by exploiting intracellular microenvironment, thus increasing the efficacy of nucleotide drugs. The present invention provides preparation methods of such polymers, which can condense DNA into polyplexes but, once inside cell, lose their positive charges to quickly release the packed DNA, thus facilitating DNA expression.

Due to the abnormal physiological characteristics of tumor, tumor tissues will generate a large amount of reactive oxygen species (ROS), including hydrogen peroxide ($H_2O_2$), superoxide anion ($O_2\cdot$), hydroxyl radicals (OH·), which can oxidize phenylboronate acid/esters into phenolic groups, thus activating the p-hydroxylmethylphenol-shedding reaction (Broaders, K. E.; Grandhe, S.; Frechet, J. M., A biocompatible oxidation-triggered carrier polymer with potential in therapeutics. J Am Chem Soc 2011, 133 (4), 756-8.). Boronate acid could form cyclic esters with diols, thus enhancing its interaction with cancerous cells or nucleotide of DNA or RNA in gene delivery. (Piest, M.; Engbersen, J. F., Role of boronic acid moieties in poly (amido amine)s for gene delivery. J Control Release 2011, 155 (2), 331-40.). Moreover, boronate acid/esters is not toxic towards human body.

The present invention presents the preparation of p-benylboronate acid/esters substituted quaternary ammonium-containing polymers, which have the ability to undergo positive to negative charge-reversal upon oxidation of the benzylboronate acid/esters group by intracellular ROS and demonstrates that such polymers are more efficiently deliver DNA and induce gene expression. There is no report on such polymer, nor its preparation method or application.

SUMMARY OF INVENTION

The present disclosure relates to cation polymers capable of removing positive their cationic charges through responding to oxidation. The cationic polymers contain positive charges of quaternary amines with p-benylboronate acid/esters. The polymer can self-assemble into stable nanocomplexes with nucleic acids mainly through electrostatic interaction. Once inside the cells, upon oxidation of the boronate acid/ester group by ROS, each quaternary ammonium eliminates a p-hydroxylmethylenephenol (HMP) molecule and becomes a tertiary amine, which further self-catalyzes hydrolysis of the ester group; the polymers become anionic polymer and thus dissociate with the nucleic acid for effective transfection.

The present invention also discloses the applications, as gene delivery carriers or vectors, of the cation polymers that capable of removing positive their cationic charges through responding to oxidation. The present invention provides highly effective, and low toxic non-virus gene carriers. The nano complex formed by DNA with such carriers has high transfection rate.

The cation polymers capable of removing positive charges through oxidative response are characterized by including the moiety as follows:

Wherein:

$R_1$ and $R_2$ are independently selected from the group consisting of $C_{1-6}$ alkyl or aryl;

$R_3$ and $R_4$ are independently selected from the group consisting of hydrogen, $C_{1-6}$ alkyl or acyl;

m is a positive integer from 1 to 4;

Anion $X^-$ is bromide or chloride ion.

preferably, the cationic polymers are obtained from the reaction between polyacrylate, polymethacrylate or other primary or secondary amino-containing polymers and the compound containing benzylboronic acid or ester.

More preferably, the primary or secondary amino-containing polymers includes poly[2-(N,N-disubstituted-amino)ethyl acrylate], polyethyleneimine (PEI) and Poly (amidoamine) dendrimers (PAMAM).

Preferably, $R_1$ and $R_2$ are methyl or ethyl groups. $R_3$ and $R_4$ are selected from hydrogen, acetyl or formyl group; m is a positive integer from 1 to 3, more preferably 1 or 2; further more preferably, 2.

Preferably, the cationic polymer is selected one or more from compound (1)-(4) as follows:

In the formula above, n is from 5 to 500, preferably 50 to 300. $R_1$ and $R_2$ are independently selected from the group consisting of $C_{1-6}$ alkyl or aryl, respectively, and preferably, ethyl is selected as a further optimization. The generation of PAMAM is selected from 2 to 5.

Preferably, compounds (1) and (2) are prepared by either methods as follows:

Method 1: Polymerization of 2-(N,N-disubstituted-amino)ethyl acrylate or 2-(N,N-disubstituted-amino)ethyl methacrylate to produces poly[2-(N,N-disubstituted-amino) ethyl acrylate] or poly[2-(N,N-disubstituted-amino)ethyl methacrylate], which is then reacted with p-bromomethylphenylboronic acid, p-bromomethylphenylboronic ester, p-chloromethylphenylboronic acid or p-chloromethylphenylboronic ester to produce the desired compound.

Method 2: 2-(N,N-disubstituted-amino)ethyl acrylate or 2-(N,N-disubstituted-amino)ethyl methacrylate first reacts with p-bromomethylphenylboronic acid, p-bromomethylphenylboronic ester, p-chloromethylphenylboronic acid or p-chloromethylphenylboronic ester to obtain the corresponding ammonium-based cationic monomer, 2-[(meth)acryloyloxy]ethyl-[p-(boronic acid)benzyl]-di-substituted ammonium bromide (or chloride) or 2-[(meth)acryloyloxy]ethyl-[p-(boronic ester)benzyl]-diethyl ammonium bromide (or chloride), which is then polymerized to produce the desired compound.

Preferably, the di-substituents are ethyl groups, giving compound (1) and (2) as follows:

Taking compound (1) as an example, its preparation method is shown in the following scheme:

Preferably, compounds (3) and (4) are prepared by the Michael addition reaction of the acrylate monomers with PEI or PAMAM. The acrylate monomers include 2-acryloyloxyethyl-[p-(boronic acid)benzyl]-di-substituted ammonium bromide (or chloride) or 2-acryloyloxyethyl-[p-(boronic ester)benzyl]-diethyl ammonium bromide (or chloride); preferably, the disubstituents are ethyl groups.

Preferably, the compound (3) is as follows:

Its manufacturing method is as follows:

Preferably, the formula of compound (4) is as follows:

Its preparation method is as follows:

The present invention discloses the cation polymers capable of removing positive charges through oxidative response. Upon oxidation by ROS, the ammonium moiety sheds off a HBA to remove the positive charge and becomes a tertiary amine, which further self-catalyzes hydrolysis of the ester into a negatively charged carboxylic group. Taking the compound (1) as an example, its process of charge-reversal is shown as follows:

The present invention also discloses the applications of the polymers capable of removing positive charges through oxidative response in DNA or oligonucleotides delivery.

The present invention also discloses the applications of these cation polymers capable of removing positive charges through oxidative response in delivery of taxol.

Compared with the existing technology, the present invention has the following beneficial effects:

(1) The polymers capable of removing positive charges through oxidative response disclosed by the invention are easily prepared with a simple construction;

(2) Different from that the conventional ammonium-based cationic gene delivery carriers (such as poly[2-(acryloyloxy) ethyltrimethyl ammonium bromide (or chloride)] condense nucleic acids to form excessively tight and stable nanocomplexes, leading to inefficient release of nucleic acid under the intracellular environment and thus low transfection efficiency, the p-(boronic acid or ester)benzyl-substituted ammonium-based cationic polymers in this invention become a tertiary amine upon oxidation of the intracellular ROS and then self-catalyze further hydrolysis of the ester into negatively charged carboxylic group, prompting the dissociation with carboxylic acid and the subsequent effective transfection;

(3) The p-(boronic acid or ester)benzyl-substituted ammonium-based cationic polymers in this invention show relatively higher transfection activities (compared with PEI 25 KDa) with lower cytotoxicity.

SPECIFIC EMBODIMENTS OF THE PRESENT INVENTION

The present invention provides several examples. However, the present invention is not limited by these specific examples.

Example 1

Synthesis of Polymer (1)

Two methods were adopted to synthesize polymer (1);
Method 1:
2-(N,N-diethylaminoethyl)acrylate (DEAEA) was distilled under reduced pressure. DEAEA (5 g) and AIBN (Azobisisobutyronitrile) (0.05 g) were mixed according to the mole ratio of 100:1, and deoxygenated at room temperature with nitrogen for 30 minutes, and then mixed and polymerized at 65° C. for 24 hours under anaerobic condition. The viscous liquid was dissolved in $CH_2Cl_2$, and precipitated in ice cold n-hexane. The resulting poly[2-(N,N-diethylaminoethyl)acrylate] (PDEAEA) was purified by re-precipitation for three times and dried under vacuum. The PDEAEA was obtained as a light yellow viscous liquid (4.5 g, yield 90%).

The molecular weight of the obtained PDEAEA was determined by gel permeation chromatography (GPC). Polyethylene glycol (PEG) standard substance or PDEAEA samples were dissolved in THF with a concentration of 10 mg/mL. After filtration with 0.22 μm filter, 10 μL of the sample was injected and the chromatogram was recorded. PDEAEA had a number-average molecular weight of 10.1 KDa, and weight-average molecular weight of 16.4 KDa and polydispersity of 1.62.

PDEAEA (0.3 g) was reacted with 4-(bromomethyl)phenylboronic acid (0.56 g,) in a mole ratio of 1:1.5 in DMF at room temperature for 24 hours. The resulting solutions were dialyzed overnight against deionized water using a dialysis bag with a molecular weight cut-off of 3,500 Da and then lyophilized by using a microporous membrane with holes of 0.22 μm to obtain the polymer (1) as a white solid (0.63 g, yield 92%) after freeze drying. The structure is shown as follows (bromide ion is omitted, similarly hereinafter):

NMR data of polymer (1) is shown as follows: $^1$H-NMR, $D_2O$: δ=7.2-8.0 (4H, ArH), δ=4.0-4.6 (4H, ArHCH$_2$N(CH$_2$CH$_3$)$_2$CH$_2$CH$_2$OOCCH—), δ=3.0-3.6 (6H, ArHCH$_2$N(CH$_2$CH$_3$)$_2$CH$_2$CH$_2$OOCCH—), δ=2.3-2.6 (1H, CH$_2$CH—), δ=0.8-1.6 (8H, ArHCH$_2$N(CH$_2$CH$_3$)$_2$CH$_2$CH$_2$OOCCH—, —CH$_2$CH—). All the tertiary amines were quaternized. N=59.

Method 2:
DEAEA (5 g) and 4-(bromomethyl)phenylboronic acid (6.25 g) was dissolved in DMF. After stirring overnight, the reaction mixture was precipitated three times in diethyl ether and dried under vacuum to yield 2-(acryloyloxy)ethyl-(p-boronic acid)benzyl-diethylammonium bromide (B-DEAEA) as a white solid (9.56 g, yield 85%). The structure is shown as follows (bromide ion is omitted):

B-DEAEA (5 g) and AIBA (0.015 g) was dissolved in water, and degased with $N_2$ for 30 min. Then the mixture was heated to 65° C. for 8 hours. The reaction mixture was then dialyzed against water for 12 hours and lyophilized to obtain a white solid (4.35 g, yield 87%) after freeze drying. The polymer with the similar degree of polymerization (n) as that in method (1) was obtained by adjusting the feeding ratio.

Synthesis of Polymer (2)

2-(N,N-diethylaminoethyl)methacrylate (DEAEMA) (10 g) and ethyl bromoisobutyrate (0.04 mL) were dissolved in 2 mL methanol in a glass ampoule and the air was removed by bubbling with $N_2$ for 30 minutes. Then CuBr (0.04 g) and bipyridine (0.088 g) in another ampoule were degassed and added. After stirring at 30° C. overnight, the resulting solution was diluted with THF and filtered through a $Al_2O_3$ column. The filtrate was concentrated and precipitated three times in cold hexane to obtain PDEAEMA as a light yellow viscous liquid (8.9 g yield 89%) with a number-average molecular weight of 9.4 KDa, and weight-average molecular weight of 12.4 KDa, where n was 51.

Following the general quaternization method in method (1), the polymer (2) with 100% quaternization ratio was obtained as a white solid (yield 90%), whose structure is shown as follows:

2

NMR data of polymer (2) is shown as follows:
$^1$H-NMR, $D_2O$: δ=7.2-8.0 (4H, ArH), δ=4.0-4.6 (4H, ArHCH$_2$N(CH$_2$CH$_3$)$_2$CH$_2$CH$_2$OOCC—), δ=3.0-3.6 (6H, ArHCH$_2$N(CH$_2$CH$_3$)$_2$CH$_2$CH$_2$OOCC—), δ=0.8-1.6 (11H, ArHCH$_2$N(CH$_2$CH$_3$)$_2$CH$_2$CH$_2$OOCCH—, CH$_3$C—, —CH$_2$C—). n=80.

Synthesis of Polymer (3)

Polymer (3) was obtained by the Michael addition of PEI and B-DEAEA. Briefly, PEI$_{10K}$ (molecular weight 10000, n=230, 1.0 g) and B-DEAEA (8.5 g) was dissolved in dry methanol. The mixture was stirred at 50° C. for 3 days under Argon atmosphere. After dialysis against water for 20 hours, polymer (3) was obtained by lyophilization as a white solid (8.3 g, yield 87%), after freeze drying. The structure is shown as follows:

3

NMR data of polymer (3) is shown as follows:
$^1$H-NMR, $D_2O$: δ=7.2-8.0 (4H, ArH), δ=4.0-4.6 (4H, ArHCH$_2$N(CH$_2$CH$_3$)$_2$CH$_2$CH$_2$OOCCH$_2$CH$_2$N—), δ=3.0-3.8 (8H, ArHCH$_2$N(CH$_2$CH$_3$)$_2$CH$_2$CH$_2$OOCCH$_2$CH$_2$N—), δ=2.3-2.6 (6H, ArHCH$_2$N(CH$_2$CH$_3$)$_2$CH$_2$CH$_2$OOCCH$_2$CH$_2$N—, —CH$_2$CH$_2$N—), δ=0.8-1.6 (6H, ArHCH$_2$N(CH$_2$CH$_3$)$_2$CH$_2$CH$_2$OOCCH$_2$CH$_2$N—). N=230.

Synthesis of Polymer (4)

Polymer (4) was obtained as a white solid with a yield of 85% by the same method above using PAMAM of generation 3 (1 g) and B-DEAEA (3.4 g). The structure is shown as follows:

4

NMR data of polymer (4) is shown as follows: $^1$H-NMR ($D_2O$): δ=7.2-8.0 (8H, ArH), δ=4.0-4.6 (4H, ArHCH$_2$N(CH$_2$CH$_3$)$_2$CH$_2$CH$_2$OOCCH$_2$CH$_2$N—), δ=3.0-3.8 (256H, ArHCH$_2$N(CH$_2$CH$_3$)$_2$CH$_2$CH$_2$OOCCH$_2$CH$_2$N—, —CONHCH$_2$CH$_2$N—, —NCH$_2$CH$_2$NHCO—), δ=2.3-2.6 (248H, ArHCH$_2$N(CH$_2$CH$_3$)$_2$CH$_2$CH$_2$OOCCH$_2$CH$_2$N—, —CONHCH$_2$CH$_2$N—, —NCH$_2$CH$_2$NHCO—, —NCH$_2$CH$_2$N—), δ=0.8-1.6 (6H, ArHCH$_2$N(CH$_2$CH$_3$)$_2$CH$_2$CH$_2$OOCCH$_2$CH$_2$N—).

Example 2: ROS-Responsiveness of Polymer (1)

Figure 1:
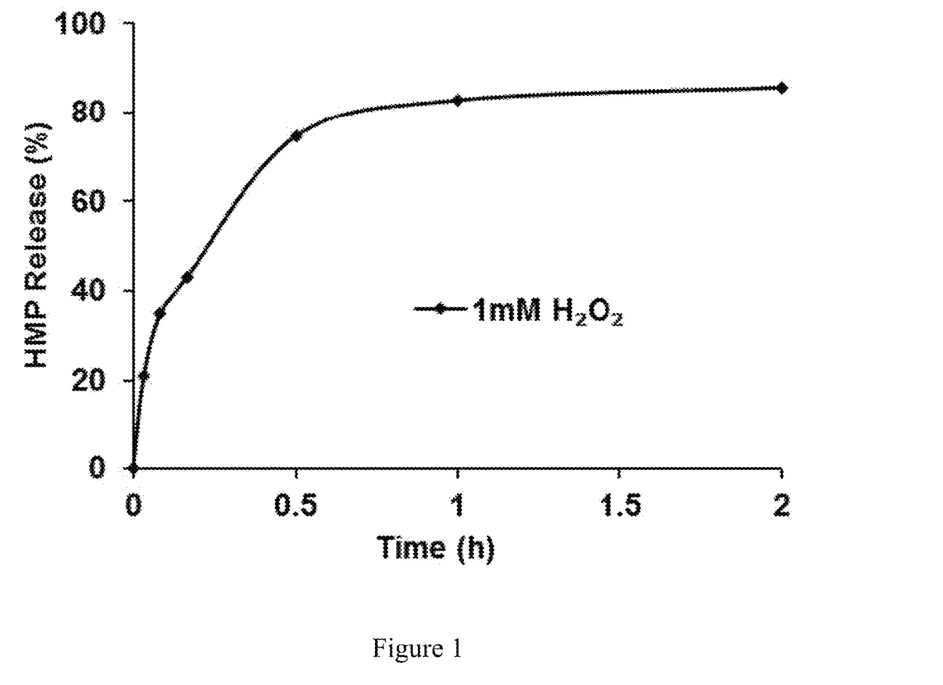
FIG. 1 shows the HMP release curve of the polymer (1) in the presence of oxidized condition as shown in Example 2.

A certain amount of polymer (1) (B-PDEAEA) was dissolved in 1 mM (mM means milimole per liter) $H_2O_2$ at a concentration of 0.3 mg/mL. The polymer (1) under the oxidized condition formed quinone, which in the water quickly became HMP (p-hydroxylmethylphenol). A Waters HPLC system was used to monitor the p-hydroxylmethylphenol (HMP) release using 10% methanol aqueous solution as eluent at a flow rate of 1.0 mL/min. Pure HMP appeared at 3.5 minutes as a standard. In 1 mM $H_2O_2$, polymer (1)

degraded quickly in the first 30 minutes and almost completely within 2 hours (FIG. 1).

Example 3: The Oxidation-Induced Charge Reversal of Polymer (1)

Solution 1: polymer (1) was dissolved in 80 mM $H_2O_2$ at a concentration of 3 mg/mL at pH 7.4 (HEPES, 10 mM). The solution was incubated at 37° C. with shaking. Samples were taken at timed intervals and their zeta potentials were measured.

Solution 2: polymer (1) was dissolved in 80 mM $H_2O_2$ at a concentration of 3 mg/mL first at pH 5.0 for 2 hours and then the solution pH was adjusted to 7.4. The solution was incubated at 37° C. with shaking. Samples were taken at timed intervals and their zeta potentials were measured.

Figure 2:
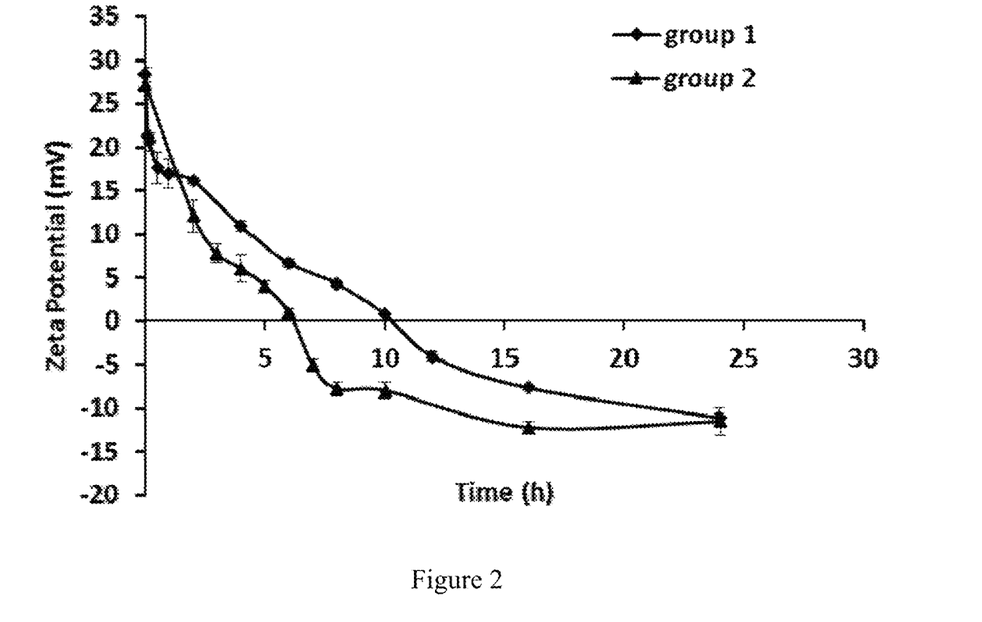
FIG. 2 shows the charge-reversal kinetics of the polymer (1) in the presence of oxidized condition as shown in Example 3.

As shown in FIG. 2, at pH 7.4, the zeta potential of polymer (1) quickly decreased from +28 to +17 mV, as the quaternary ammonium turned into a tertiary amine triggered by $H_2O_2$. Then the zeta potential decreased gradually as the ester group underwent self-catalyzed hydrolysis and produced poly(acrylic acid). The zeta potential became negative in ~10 hours. The charge-reversal was much faster, in less than 6 hours, if B-PDEAEA was first incubated at pH 5.0 with $H_2O_2$ for 2 hours and then at pH 7.4 because the oxidation potential of $H_2O_2$ is higher in acidic solution.

Example 4: Polymer (1)/DNA Polyplex Fabrication

Polymer (1) was dissolved in HEPES buffer solution (10 mM, pH=7.4) at a concentration of 1 mg/mL (denoted as polymer (1) solution), and the plasmid DNA was diluted with HEPES buffer solution to 40 µg/mL (denoted as DNA solution). The polymer (1) solutions were added with the DNA solution of the same volume and vortexed for 10 seconds to produce the polyplexes at desired N/P ratios, defined as the molar ratio of nitrogen atoms in the polymer (1) to phosphate units of the plasmid DNA. The polyplex solutions were incubated at room temperature for 30 min before characterizations.

Figure 3:
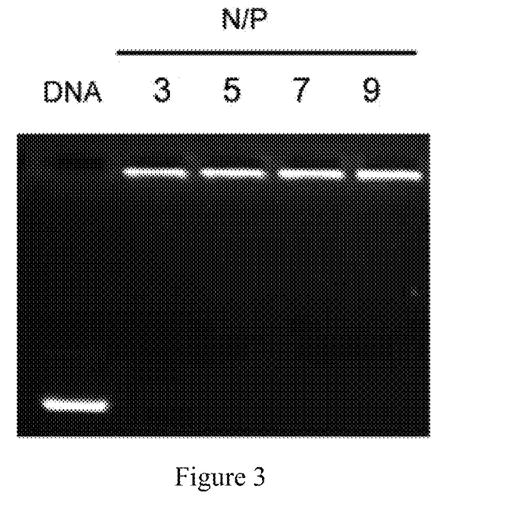
FIG. 3 shows the agarose gel electrophoresis of polymer (1)/DNA polyplexes as shown in Example 4.

The characterizations of the obtained polyplex solutions:
1. Agarose Gel Retardation Assay DNA binding ability was evaluated by agarose gel retardation assay. 20 µL of the polyplexes with a series of N/P ratio (N/P ratio at 3, 5, 7, 9) were electrophoresed on a 0.8% agarose gel (containing 0.5 mg/mL ethidium bromide) with 1×TAE buffer at 100 mV for 30 min. DNA bands were visualized by staining with ethidium bromide (EB) excited by UV transillumination. As shown in FIG. 3, the polymer (1) effectively condensed plasmid DNA at N/P ratios of above 3, thus retarding migration of DNA.

2. The Size and Zeta Potential Determination

Figure 4:
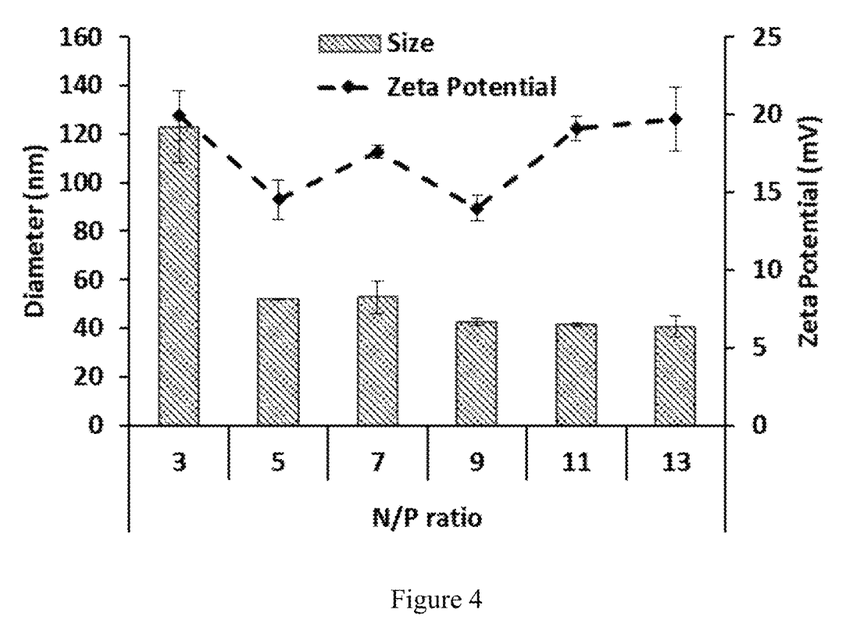
FIG. 4 shows the volume-averaged sizes and zeta potentials of polymer (1)/DNA polyplexes as shown in Example 4.

The size, zeta potentials and aggregation properties of polyplexes with a series of N/P ratios (N/P ratio at 3, 5, 7, 9, 11, 13) were measured by dynamic light scatter. Each samples was measured three times at 25° C. Data are processed by DTS software and presented as the means±SD (n=3). As shown in FIG. 4, The polymer (1) condensed plasmid DNA and formed spherical polyplexes of ≈40 nm in diameter with a zeta potential of +15 to +20 mV.

Figure 5:
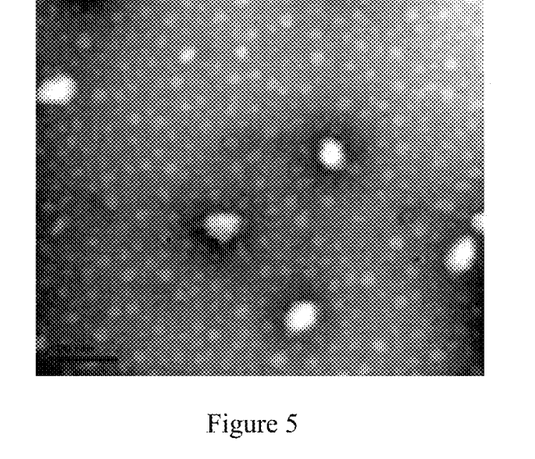
FIG. 5 shows the morphology of polymer (1)/DNA polyplexes at an N/P ratio of 13 observed by TEM in Example 4.
Figure 6:
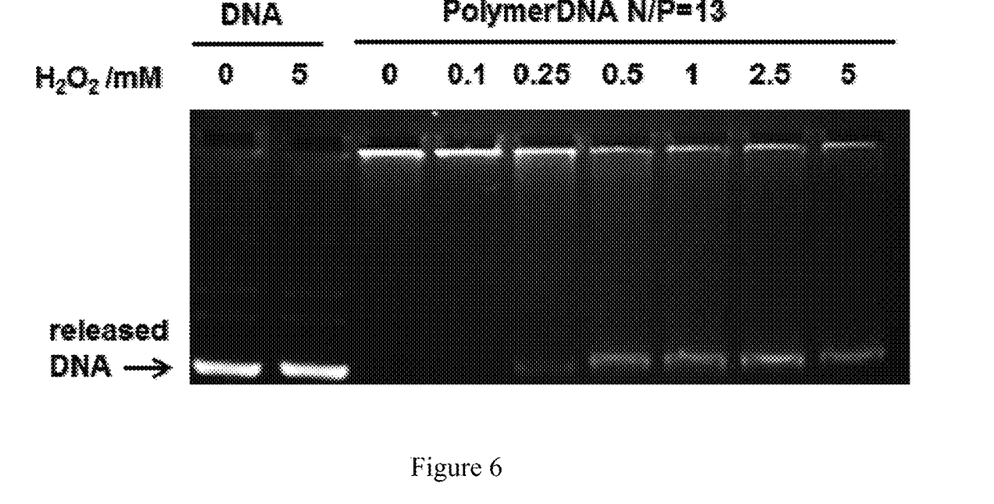
FIG. 6 shows the gel retardation assay of DNA released from polymer (1)/DNA polyplexes at an N/P ratio of 13 after 1 hour incubation in $H_2O_2$ solution at different concentrations at 37° C. in Example 4.

3. Observation of Polymer (1)/DNA Polyplex Under Transmission Electron Microscope One drop of the prepared polymer (1)/DNA polyplex at an N/P ratio of 13 was put on the 400 mesh grid. After negatively stained with phosphotungstic acid, The morphology of polyplexes was visualized using a transmission electron microscope (TEM) (JEM-1200EX). As shown in FIG. 5, electrostatic self-assembly of polymer (1) and DNA formed uniform spherical polyplexes of ≈40 nm in diameter, in line with the results of DLS.
4. Agarose Gel Retardation Assay of Polymer (1)/DNA Polyplexes at Oxidative Condition Polyplexes at an N/P ratio of 13 (20 µL) were incubated at different $H_2O_2$ concentrations for 1 hour at 37° C. Naked DNA and DNA incubated at 5 mM $H_2O_2$ were used as controls. The solutions were then electrophoresed on a 0.8% agarose gel (containing 0.5 mg/mL ethidium bromide) with 1×TAE buffer at 100 V for 30 min. DNA bands were visualized by staining with ethidium bromide (EB) excited by UV transillumination. As shown in FIG. 6, polyplexes released the DNA after 1 hour in $0.5 \times 10^{-3}$ M $H_2O_2$.

Example 5

Cytotoxicity of Polymers (1)-(4)

Figure 7:
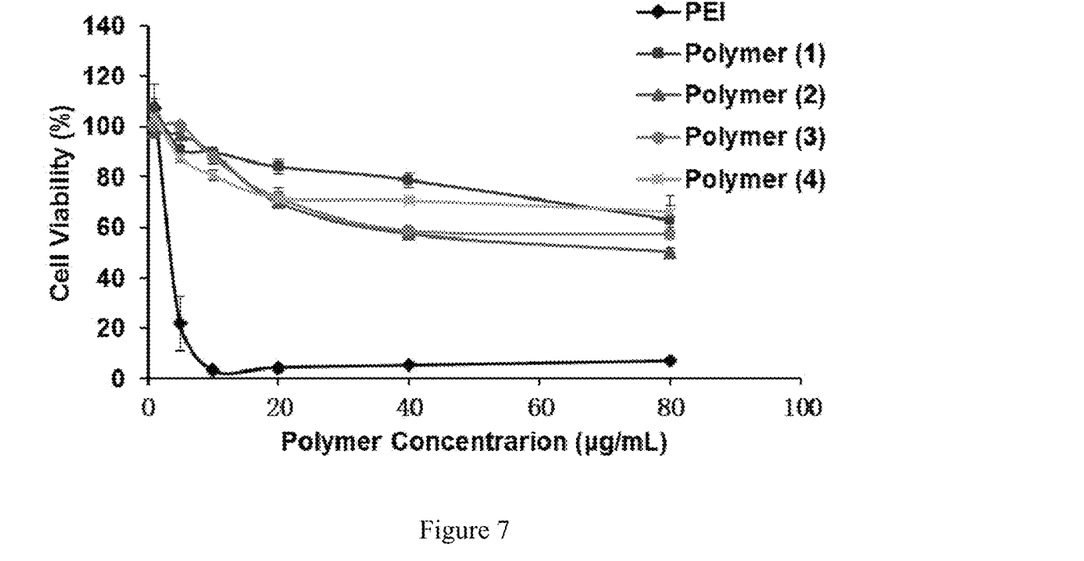
FIG. 7 shows the cytotoxicity assay of the polymers at various polymer concentrations as shown in Example 5.

The cytotoxicity of polymer (1) on A549 cells was determined by 3-(4,5-dimethylthiazol-2-yl)-2,5-diphenyltetrazolium bromide (MTT) assay. Cells were seeded in 96-well plates at a density of 5000 cells per well in 100 µL of 10% FBS and 1% penicillin-streptomycin-containing cell culture medium and incubated for 24 hours in a humidified atmosphere of 5% $CO_2$ at 37° C. PEI (25 KDa) was used as control. 100 µL of polymer solutions (5 mg/ml, 10 mg/ml, 20 mg/ml, 40 mg/ml, 80 mg/ml) or 100 µL of culture medium for blank were added and further incubated for 48 h. The plates were centrifuged at 1100 rpm for 6 minutes and the medium in each well was replaced with MTT solution (0.75 mg/mL). After 3 hours incubation, the plates were centrifuged at 2800 rpm for 7 minutes and the medium in each well was replaced with 100 µL DMSO to dissolve the formazancrystals. The absorbance was detected at 562 nm and 620 nm using a microplate spectrophotometer. The cell viability (%) was described as absorbance (experiment)/absorbance (blank). Each drug concentration was tested in triplicate and in three independent experiments. As shown in FIG. 7, polymer (1) had increased toxicity on A549 cells as the concentration increased, and a higher cell viability than PEI (25 KDa) at the same concentrations.

The cytotoxicity of polymer (2)-(4) on A549 cells was determined by the same method. As shown in FIG. 7, polymer (2)-(4) had increased toxicity on A549 cells as the concentration increased, and a much higher cell viability than PEI (25 KDa) at the same concentrations.

Example 6

In Vitro Gene Transfection of Polymer (1)-(4)/DNA Polyplexes (1) Luciferase Gene Transfection For luciferase gene transfection, plasmid DNA expressing Luciferase, pGL4.13 (Promega) was used. A549 cells were seeded in 48-well plates at a density of 25000 cells per well in 400 µL of 10% FBS containing cell culture medium and incubated for 24 hours in a humidified atmosphere of 5% $CO_2$ at 37° C. The medium was replaced with 400 µL of fresh medium (with 0%, or 10% FBS). Polymer (1)-(4)/DNA polyplexes solutions (50 µL) were added at a dose of 1 µg DNA per well and the cells were cultured for 4 h. The transfection medium was then replaced with 400 µL of fresh RPMI-1640 medium supplemented with 10% FBS. The cells were incubated for an additional 44 hours. The medium was replaced with 100 µL of 1× cell lysis buffer and centrifuged. The supernatant was separated and luciferase substrate was added to determine the chemiluminescence intensity. Protein content of the cell-lysis solution was determined by Bradford protein assay kit. The chemiluminescence intensity was normalized with respect to the protein concentration (relative luciferase light units per milligram protein). All data are presented as the mean of at least three independent measurements and each measurement was performed in triplicate.

Figure 8:
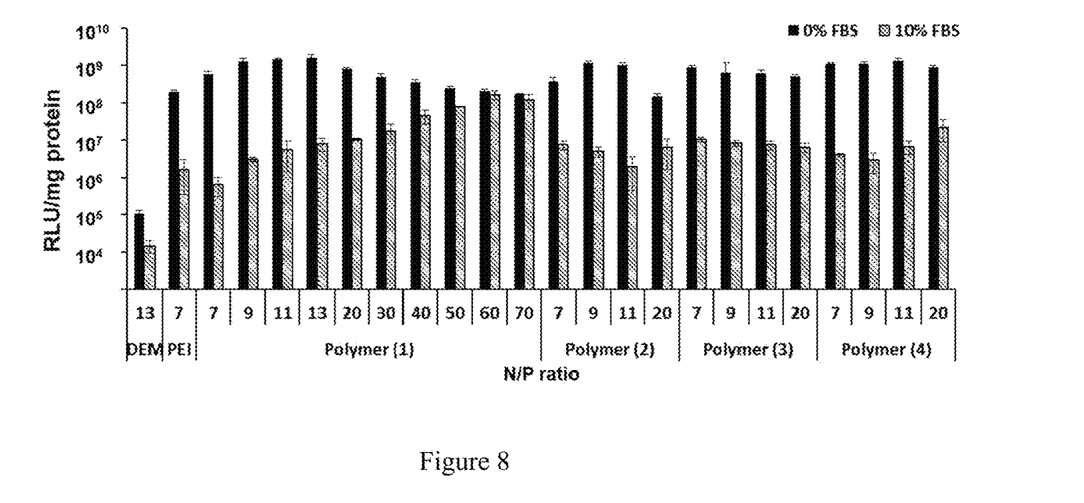
FIGS. 8-10 shows the cell transfection effects of the nano-complex formed between polymers capable of removing positive charges through oxidative response and DNA in Example 6.

As shown in FIG. 8, in the serum-free medium, the highest luciferase transfection efficiency of polymer (1)/DNA polyplexes was achieved at an N/P ratio of 13, at which the transfection efficiency was 15400 times higher than that the control ammonium-based polymer, poly[2-(N,N-diehylmethylamino)ethyl acrylate] (DEM), which is known to tightly pack DNA and have low intracellular dissociation, suggesting that the ROS-triggered charge reversal did play an important role in gene transfection. This transfection efficiency was also eight times higher than that of the gold standard of cationic polymer gene delivery carriers, branched PEI with a molecular weight of 25 KDa at an N/P ratio of 7. Notably, the polymer (1)/DNA polyplexes at N/P ratios greater than 60 were not sensitive to serum any more, whose transfection efficiency was only slightly lower than the maximum transfection without serum and ≈100 times higher than that of PEI/DNA polyplexes under the same conditions.

(2) EGFP Gene Transfection

A549 cells were seeded in 24-well plates at a density of 80,000 cells per well in 0.8 mL of 10% FBS-containing cell culture medium and incubated for 24 hours in a humidified atmosphere of 5% $CO_2$ at 37° C. The medium was replaced with 0.8 mL of fresh medium (with 0%, or 10% FBS). Polymer (1)/DNA polyplexes solutions at an N/P ratio of 13 or 60 (100 µL) were added at a dose of 4 µg DNA per well and cultured for 4 h. Then, the transfection medium was replaced with 0.8 mL of fresh RPMI-1640 medium supplemented with 10% FBS. The cells were incubated for an additional 44 hours. The medium was removed and the cells were rinsed with PBS, detached by 0.25% Trypsin/0.03% EDTA, isolated, washed twice with PBS and resuspended in 500 µL of PBS. The expression efficiency of EGFP plasmid in terms of the percentage of GFP-positive cells was quantitatively measured using flow cytometry (BD FACS Calibur™) (10,000 cells were counted per treatment). The excitation and emission wavelength of EGFP was 488 nm and 510-540 nm, respectively. PEI/DNA polyplexes were used as positive control and the untreated cells were used as negative control. All data are presented as the mean of at least three independent measurements and each measurement was performed in triplicate.

Figure 9:
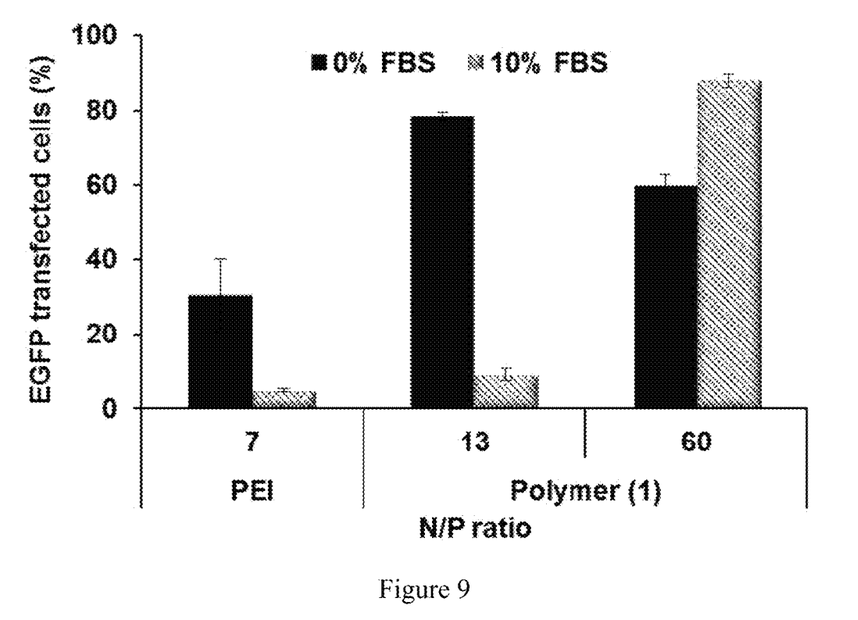

As shown in FIG. 9, in the serum-free medium, polymer (1)/DNA polyplexes at an N/P ratio of 13 transfected 78.4% cells, higher than that of PEI/DNA polyplexes (30.7%). In the medium with 10% serum, the polymer (1)/DNA polyplexes at an N/P ratio of 13 were no longer efficient and the PEI/DNA polyplexes could only transfected 5.0% of the cells; however, the polymer (1)/DNA polyplexes at high N/P ratios (N/P=60) could still transfected 90.0% cells.

(3) Observation of EGFP Expression by Confocal Microscope

To observe the expression of EGFP, A549 cells were plated onto glass-bottom petri dishes at 250,000 cells per dish in 1.5 mL of 10% FBS-containing cell culture medium and incubated for 24 h in a humidified atmosphere of 5% $CO_2$ at 37° C. The medium was replaced with 1.5 mL of fresh medium (with 0%, or 10% FBS). Polymer (1)/DNA polyplexes solutions at an N/P ratio of 13 or 60 (300 µL) were added at a dose of 6 µg DNA per well and cultured for 4 hours. Polyplex solutions (300 µL) were added at a dose of 6 µg DNA per dish and cultured for 4 hours. Then, the transfection medium was replaced with 1.5 mL of fresh medium supplemented with 10% FBS. The cells were incubated for an additional 44 hours. The images were then acquired using a confocal laser scanning microscope (CLSM, Nikon-A1 system, Japan). The excitation and emission wavelength of EGFP was 488 nm and 510-540 nm, respectively. The imaging parameters were kept constant for different groups.

Figure 10:
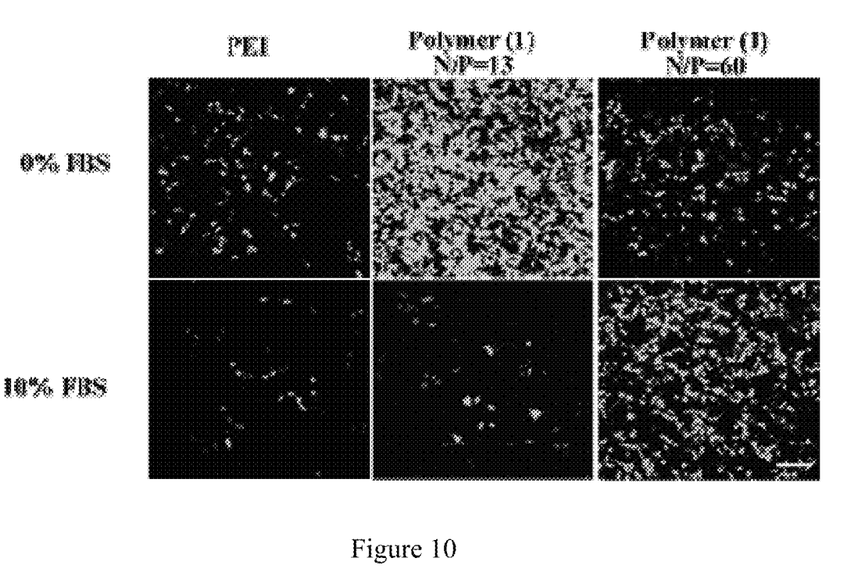

As shown in FIG. 10, in the presence of serum PEI/DNA polyplexes transfected few cells, whereas the polymer (1)/DNA polyplexes transfected cells more and uniformly. To achieve high therapeutic efficacy in cancer gene therapy, it is more desirable for all of the cells to express an amount of therapeutic protein sufficient to induce apoptosis than for a few cells to express a large amount of the protein.

Example 7: Luciferase Gene Transfection of Polymer (1)/DNA Polyplexes with the ROS Inhibitor Diphenyleneiodonium (DPI)

A549 cells were seeded in 48-well plates at a density of 25,000 cells per well in 0.4 mL of 10% FBS-containing cell culture medium and incubated for 24 hours in a humidified atmosphere of 5% $CO_2$ at 37° C. The medium was replaced with 0.4 mL of fresh medium containing DPI of different concentrations and incubated for 30 minutes. Polymer (1)/DNA polyplexes solutions at an N/P ratio of 13 (50 µL) were added at a dose of 1 µg DNA per well and cultured for 4 hours followed by replacing the transfection medium fresh RPMI-1640 medium containing 10% FBS and DPI at the indicated concentrations. The cells were incubated for an additional 6 hours. The medium was replaced with 100 µL of 1× cell lysis buffer and centrifuged. The supernatant was separated and luciferase substrate was added to determine the chemiluminescence intensity. Protein content of the cell-lysis solution was determined by Bradford protein assay kit. The chemiluminescence intensity was normalized with respect to the protein concentration (relative luciferase light units per milligram protein). All data are presented as the mean of at least three independent measurements and each measurement was performed in triplicate.

Figure 11:
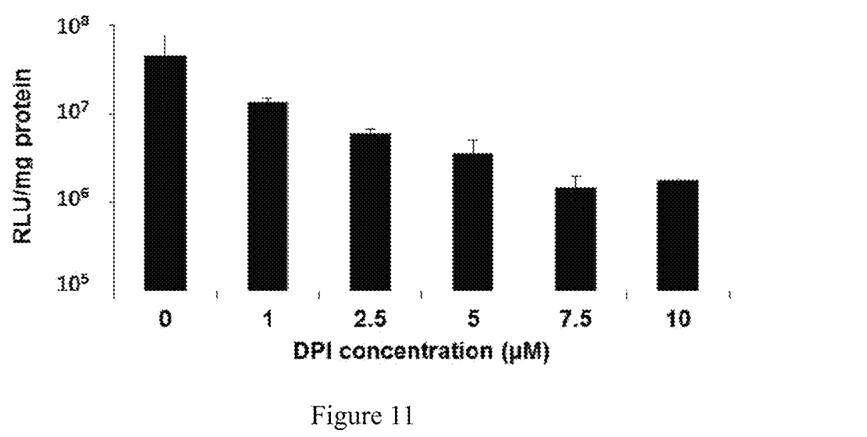
FIG. 11 shows the luciferase expression of polymer (1)/DNA polyplexes in cells pretreated with ROS inhibitor diphenyleneiodnium (DPI) without serum in Example 7.

As shown in FIG. 11, the luciferase gene expression in the DPI-treated cells decreased by up to two orders of magnitude, indicating that without ROS the polyplexes could not release the plasmids efficiently for transfection.

Example 8: In Vivo Gene Transfection by Intratumor Injection of Polymer (1)/DNA Polyplexes Female BALB/c athymic mice (6-8 weeks old) were subcutaneously inoculated of 5×10⁶ A549 cells in the right flank region. When the tumor volumes reached ~200 $mm^3$, the tumor bearing mice were randomly divided into 2 groups (n=6). Polymer (1)/DNA (N/P=13) or PEI/DNA polyplex (N/P=7) containing 15 µg luciferase DNA in 60 µL was injected into the tumor. At 48 hours post-injection, the tumors were harvested and homogenized in cell lysis buffer. The samples were centrifuged (13,500 g, 10 min) at 4° C. The supernatant was separated and the luciferase substrate was added to determine the chemiluminescence intensity. The protein content of the cell-lysis solution was determined by Bradford protein assay kit. The chemiluminescence intensity was normalized with respect to the protein concentration (relative luciferase light units per milligram protein).

Figure 12:
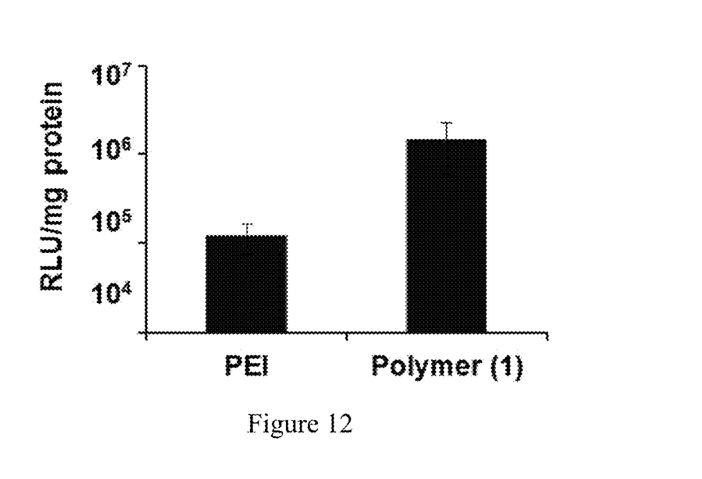
FIG. 12 shows the in-tumor injection of luciferase transfection of polymer (1)/DNA polyplexes in Example 8.

As shown in FIG. 12, the luciferase expression in the tumor at 48 hours post-injection of polymer (1)/DNA polyplexes with an N/P ratio of 13 was ≈12 times higher than the positive control PEI polyplexes, indicating that polymer (1)/DNA polyplexes would efficiently transfect tumor cells once arriving tumor tissue.

In summary, the gene delivery carrier capable of reversing charges through oxidative response constructed in accordance with the present invention is highly positively charged and can adequately encapsulate DNA, and can enter into cells and then undergo the action of active oxygen free radicals within the cell. The charges reverse from positive to negative and escape from lysosomes, releasing DNA to the nucleus for transfection. The carrier has high transfection activity and low cytotoxicity, and has a good application prospect.

What is claimed is:

1. A cationic polymer capable of removing positive charges through oxidative response, comprising the following moiety:

wherein:

$R_1$ and $R_2$ are independently selected from the group consisting of $C_{1-6}$ alkyl or aryl;

$R_3$ and $R_4$ are independently selected from the group consisting of hydrogen, $C_{1-6}$ alkyl or acyl; and m is a positive integer from 1 to 4;

wherein the cationic polymer is obtained from reactions between polyacrylate, polymethacrylate or other primary or secondary amino-containing polymers and a compound containing benzylboronic acid or ester; and wherein the primary or secondary amino-containing polymers comprise poly[2-(N,N-disubstituted-amino)ethyl acrylate], polyethyleneimine (PEI) and poly(amidoamine) dendrimers (PAMAM).

2. The cationic polymer of claim 1, wherein $R_3$ and $R_4$ are selected from hydrogen, acetyl or formyl, and $R_1$ and $R_2$ are methyl or ethyl.

3. The cationic polymer of claim 1, wherein the polymer is used for the delivery of deoxyribonucleic acids and oligonucleotides.

4. The cationic polymer of claim 1, wherein the polymer is used for the delivery of taxol.

5. The polymer of claim 1, wherein the polymer comprises an anion, which is bromide or chloride ion.

* * * * *